US012721733B2

(12) United States Patent
Innamorato et al.

(10) Patent No.: US 12,721,733 B2
(45) Date of Patent: Sep. 1, 2026

(54) INJECTABLE TISSUE REPAIR DEVICES AND PROCESSES FOR PREPARATION THEREOF

(71) Applicant: DSM IP Assets B.V., Heerlen (NL)

(72) Inventors: Julia Innamorato, Columbia, MD (US); Rachel Dichter, Columbia, MD (US); Nicholas Roscioli, Columbia, MD (US); Andrew Hall, Columbia, MD (US)

(73) Assignee: DSM IP Assets B.V. (NL)

( * ) Notice: Subject to any disclaimer, the term of this patent is extended or adjusted under 35 U.S.C. 154(b) by 316 days.

(21) Appl. No.: 18/278,207

(22) PCT Filed: Feb. 23, 2022

(86) PCT No.: PCT/US2022/017409
§ 371 (c)(1),
(2) Date: Aug. 22, 2023

(87) PCT Pub. No.: WO2022/182692
PCT Pub. Date: Sep. 1, 2022

(65) Prior Publication Data

US 2024/0122726 A1 Apr. 18, 2024

Related U.S. Application Data

(60) Provisional application No. 63/152,616, filed on Feb. 23, 2021.

(51) Int. Cl.
*A61F 2/46* (2006.01)
*A61B 17/88* (2006.01)
(Continued)

(52) U.S. Cl.
CPC ........ *A61F 2/4601* (2013.01); *A61B 17/8833* (2013.01); *A61L 27/24* (2013.01);
(Continued)

(58) Field of Classification Search
CPC .......... A61F 2/46; A61F 2/4601; A61B 17/88; A61B 17/8833; A61L 27/24; A61L 27/56;
(Continued)

(56) References Cited

U.S. PATENT DOCUMENTS 7,824,703 B2 11/2010 Scifert et al.
8,551,514 B2 10/2013 Ringeisen et al.
(Continued)

OTHER PUBLICATIONS

International Search Report and Written Opinion dated May 25, 2022.

*Primary Examiner* — Christopher J Beccia
(74) *Attorney, Agent, or Firm* — Kevin M. Bull

(57) ABSTRACT

Disclosed are tissue repair devices, processes for preparing such devices, and methods of use of such devices. In an embodiment, a tissue repair device comprises porous, compressible pellets of a tissue repair material that may be provided and then hydrated in the barrel of a syringe. In an embodiment, the tissue repair material is configured in the barrel of the syringe such that an elongate channel is present, the channel being defined by the interior wall of the barrel and the tissue repair material.

23 Claims, 3 Drawing Sheets

(51) Int. Cl.

| | |
|---|---|
| ***A61L 27/24*** | (2006.01) |
| ***A61L 27/44*** | (2006.01) |
| *A61B 17/00* | (2006.01) |
| *A61B 17/56* | (2006.01) |

(52) U.S. Cl.
CPC ..... *A61L 27/44* (2013.01); *A61B 2017/00526* (2013.01); *A61B 2017/564* (2013.01); *A61B 2017/8838* (2013.01); *A61L 2430/02* (2013.01)

(58) Field of Classification Search
CPC ........ A61L 27/44; A61L 27/42; A61L 27/425; A61M 5/31; A61M 5/3129
See application file for complete search history.

(56) References Cited

U.S. PATENT DOCUMENTS

| | | | | |
|---|---|---|---|---|
| 10,194,964 | B2 | 2/2019 | Schlachter et al. | |
| 2003/0236573 | A1* | 12/2003 | Evans | A61F 2/4601 623/23.63 |
| 2020/0405364 | A1* | 12/2020 | Shimko | B01F 35/3202 |

* cited by examiner

INJECTABLE TISSUE REPAIR DEVICES AND PROCESSES FOR PREPARATION THEREOF

CROSS-REFERENCE TO RELATED APPLICATIONS

This application is a U.S. national phase entry under 35 USC § 371 of International Application No. PCT/US2022/017409, filed 23 Feb. 2022, which claims priority to U.S. Provisional Patent Application No. 63/152,616 on 23 Feb. 2021, the entire contents of each of which is expressly incorporated herein by reference.

FIELD

The disclosed inventions pertain to injectable tissue repair devices, processes for preparing such devices, and methods of use of such devices. The tissue repair devices may be useful for repairing defects in bone.

BACKGROUND

Medical articles for repairing tissue defects come in various forms and have various uses. One such medical article is a bone void filler in the form of a three-dimensional sponge. The sponge is typically in the form of a lyophilized composition of natural polymer(s). The sponge may be hydrated, which makes it pliable. The hydrating fluid may take various forms. Examples of the hydrating fluid are sterile water, whole blood, platelet rich plasma (PRP), and bone marrow aspirate. Once made pliable, the material may be placed into a bone defect directly by hand or placed into a syringe and dispensed into a bone defect.

Such sponges are typically formed by first forming a slurry comprising water and particles or fibers of a biocompatible polymer. The slurry may further comprise a mineral, such as a mineral known to promote bone growth. Examples of such minerals are hydroxyapatite, calcium phosphates, bioactive glasses, bone particles, and mixtures thereof. The slurry is dispensed into a mold. The mold and slurry together are then placed in a freeze-dryer and the slurry lyophilized, resulting in a sponge. The sponge is then separated from the mold. Post-processing, such as machining to ensure suitable surface smoothness, may be carried out prior to packaging and sterilization.

An advancement in medical articles for treating tissue defects over the years has been improving the ease of use. One such advancement is to provide the medical article in a form that allows the treating doctor to easily hydrate the medical article. One such commercially available product is MASTERGRAFT® Putty by Medtronic®. The product is a dish-shaped sponge made of a lyophilized composition of approximately 80 wt % mineral and 20 wt % of Type I bovine collagen. The mineral is in the form of particles present throughout the sponge. The mineral particles comprise approximately 15 wt % of hydroxyapatite and 85 wt % of β-tricalcium phosphate, based on the total weight of the particles.

The MASTERGRAFT® Putty sponge is in the form of a dish, having a reservoir that may hold the hydrating fluid. The reservoir is formed by a perimeter sidewall and a recessed surface. The article has a rectangular cross-section. To use the material, the doctor dispenses the prescribed amount of hydrating fluid directly into the dish. This has the advantage that the correct amount of hydrating fluid is used and that the hydrating fluid does not run off the sponge onto other surfaces. The doctor then manipulates the material to uniformly hydrate the sponge with the hydrating fluid, either manually or with the aid of tools.

Further such medical articles are disclosed in U.S. Pat. No. 7,824,703. This publication describes medically useful articles comprising a three-dimensional body including one or more implantable substances, wherein the body defines one or more reservoirs for receiving amounts of a biocompatible wetting liquid. In certain embodiments the body is disruptable upon wetting with the biocompatible liquid to form a conformable implantable material such as a putty, paste or more flowable wetted implant material.

Once adequately hydrated, the above-mentioned tissue repair devices are either inserted into the tissue defect by hand or with the aid of a syringe. Use of a syringe may enable more accurate placement of the tissue repair device by the surgeon, especially when the tissue defect is concave or a narrow fissure. Accordingly, many surgeons prefer to insert the hydrated tissue repair device into the tissue defect via syringe.

SUMMARY

One drawback of the above-mentioned tissue repair devices is that significant handling of the tissue repair devices is required prior to insertion into the tissue defect. For example, the hydrating fluid must first be measured and dispensed onto the tissue repair device. Second, the hydrating fluid must be worked into the tissue repair device in order to adequately and uniformly hydrate it. Next, the hydrated tissue repair device is placed into the barrel of a syringe, potentially tamped down, and then dispensed into the tissue defect.

Besides being inconvenient and potentially increasing time in the operating room, the handling may introduce contamination. Additionally, material may be lost when preparing the tissue repair device or inserting the hydrated tissue repair device into the syringe. A tissue repair device that can be stored in, hydrated in, and dispensed from a single syringe would therefore be desirable.

In an embodiment, a method for forming a tissue repair device comprises the steps of:

a. providing a syringe comprising a barrel in fluid communication with a tip, the barrel comprising an interior wall and at least one elongate obstruction extending over a length of the barrel, the obstruction being in contact with or proximate to the interior wall;
b. inserting into the barrel a plurality of porous, compressible pellets of a tissue repair material, the tissue repair material being extrudable via the tip upon hydration; and
c. removing the obstruction.

The pellets of tissue repair material are porous and compressible. Due to their porous and compressible nature, the pellets will stay in a compressed state after removal of the compressive force. Furthermore, the compressed material will not substantially fill the void created by removing the obstruction. In an embodiment, at least some of the plurality of pellets are compressed prior to removing the obstruction.

Upon removing the obstruction there is a void present in the form of a channel along the length of the syringe adjacent the interior wall where the obstruction had been located. The channel is defined by the syringe's interior wall and the tissue repair material. The tissue repair material may then be hydrated by dispensing a hydrating fluid, such as saline solution or blood, into the channel and mixing. After suitable mixing, the tissue repair material is extrudable from the tip, such as in the form of a flowable solution, gel, paste, or putty.

The use of channels as described herein may allow for more material to be contained within the barrel than if an obstruction was required to be retained in the barrel during shipping or hydrating. The described devices may also weigh less and produce less waste.

Superior results may be obtained by hydrating via the channel described above as opposed to via a channel that is defined on all sides by the tissue repair material. For example, the inventors have found that the tissue repair material may possess superior features, such as improved injectability, more uniform hydration, and superior handling. Moreover, the disclosed embodiments may allow for hydration via the tip such as by, for example, connecting a second syringe of hydrating fluid to the tip of the syringe. The process of forming an injectable tissue repair material may also be improved over the prior art, such as by increasing speed or consistency, or reducing physical exertion. In certain embodiments, mixing of hydrating fluid and tissue repair material is not required, thereby allowing for a fully formed product where the only step required to prepare the extrudable tissue repair material is to hydrate via the tip.

Further disclosed are tissue repair devices. In an embodiment, a syringe comprising a barrel in fluid communication with a tip, the barrel comprising an interior wall and a porous, compressed tissue repair material present in the barrel, wherein the tissue repair device is configured such that there is at least one elongate channel extending over a length of the barrel through the tissue repair material, wherein the channel is defined by the interior wall and the tissue repair material.

In a further embodiment, the tissue repair device may comprise an obstruction which is intended to be removed by the surgeon just prior to hydrating the device. Such tissue repair device may comprise compressed or uncompressed tissue repair material. If uncompressed, the surgeon should compress the tissue repair material and subsequently remove the obstruction prior to hydrating. Accordingly, in an embodiment a tissue repair device comprises a syringe comprising a barrel in fluid communication with a tip, the barrel comprising an interior wall, a porous tissue repair material present in the barrel, and an elongate obstruction in contact with the interior wall and otherwise surrounded by tissue repair material. In an embodiment, the tissue repair material is present as pellets. In a further embodiment, the tissue repair material is compressed.

The tissue repair device may be used by hydrating the tissue repair material and injecting it. In an embodiment, a tissue defect in a human or animal body may be treated by performing the following steps:

a. providing a syringe comprising a barrel in fluid communication with a tip, the barrel comprising an interior wall, tissue repair material, and at least one elongate channel extending over a length of the barrel, the channel being defined by the interior wall and the tissue repair material, wherein the tissue repair material is porous and compressed;
b. inserting a hydrating fluid into the channel to form an extrudable tissue repair material.

The method may further comprise the step of extruding the extrudable tissue repair material into the tissue of a human or animal body, for instance, by injecting from the syringe.

Various further benefits may be obtained by applying the processes and forming the tissue repair devices described herein, including fewer part defects, lower scrap rates, increased manufacturing throughput, lower manufacturing costs, reduced post-processing time, greater flexibility of material composition and mineral loading in the slurry, improved mechanical properties of the tissue repair material, more consistency in final handling properties after hydration, a lower likelihood of leaking fluids, improved ease of use.

DETAILED DESCRIPTION

Figure 1:
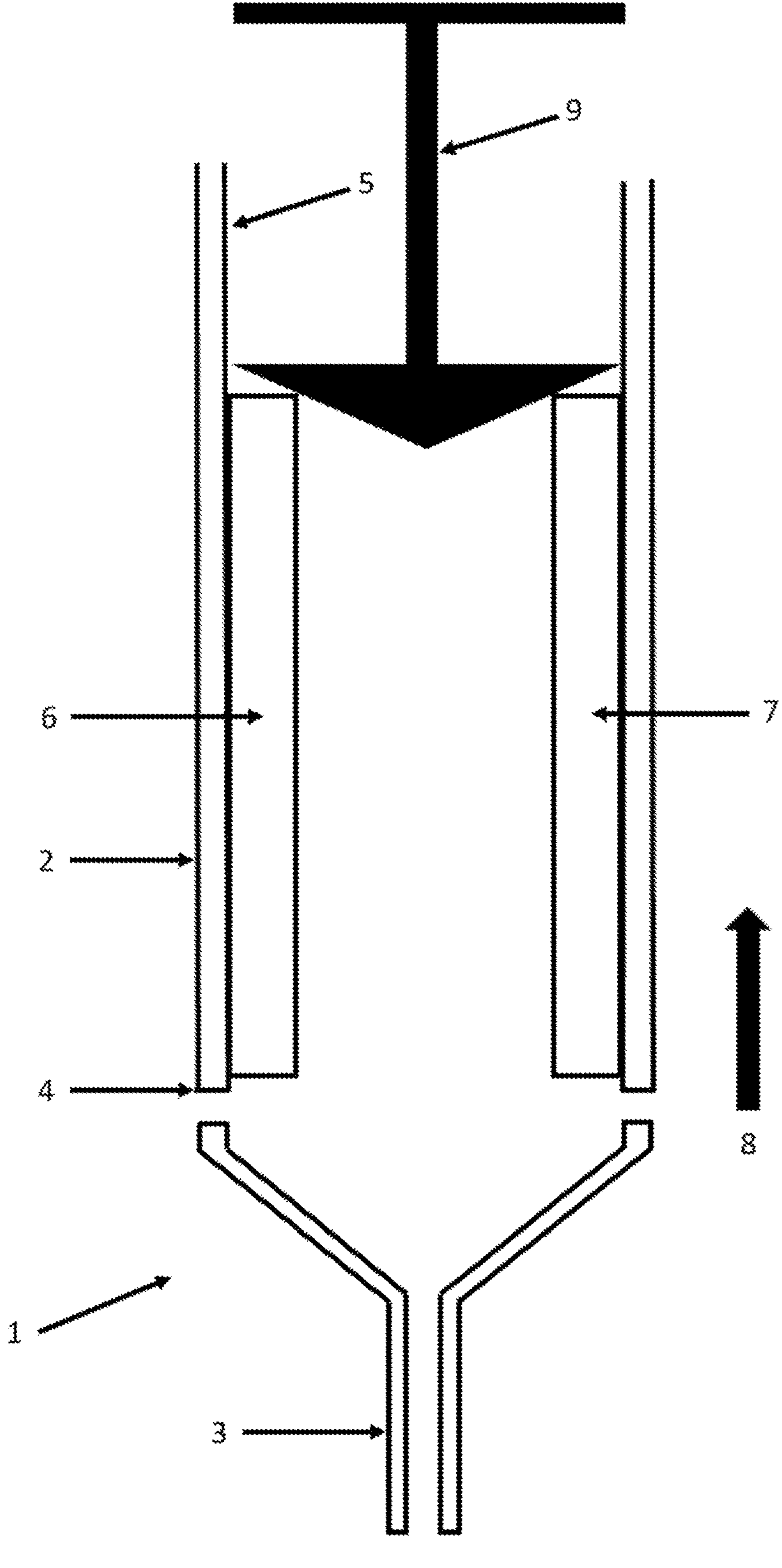
FIG. 1 is a depiction of a side view of a syringe comprising an obstruction.

Throughout this application, the term tissue repair material refers to the tissue repair material prior to it being hydrated with a hydrating fluid. Such a tissue repair material is typically not extrudable or very poorly extrudable through the tip of the syringe. When the term extrudable tissue repair material, flowable tissue repair material, or hydrated tissue repair material is used, the terms refer to a tissue repair material after being hydrated by combining with a hydrating fluid and mixing the tissue repair material and the hydrating fluid.

The term tissue repair device refers to a medical device comprising a tissue repair material. In an embodiment, the methods and tissue repair devices described herein comprise a syringe. The syringe may possess any suitable form and typically comprise a barrel and a tip. The tip may be a needle, but due the flow properties of a typical tissue repair material in its hydrated state, low gauge tips (larger diameter) are likely most suitable.

In an embodiment, the barrel of a syringe is used to prepare the tissue repair material for injection. The barrel is typically circular in cross section and cylindrical or frustoconical in shape. Suitable barrel sizes typically depend on the diameter of the tip and the amount of tissue repair material needed. After preparation of the tissue repair material, a plunger may be inserted into the proximal end of the barrel and the extrudable tissue repair material extruded from the tip.

The tissue repair material is porous. Pores can be formed by numerous methods, including via the use of gas, liquid, or a thermally labile porogen that is removed from the tissue repair material, leaving behind a pore. For example, a tissue repair material may be degassed via vacuum, creating pores as gas is expanded within the tissue repair material due to the decrease in pressure. In an embodiment, pores are formed in a tissue repair material by lyophilizing a slurry, in which case liquid (typically water) acts as the porogen.

In an embodiment, the tissue repair material comprises porous, compressible pellets. In an embodiment, the pellets comprise a sponge. A suitable sponge may be formed by filling a mold with a slurry and lyophilizing the slurry in the mold, as described herein. In an embodiment, the slurry comprises water and polymer fibers. The polymer fibers are preferably fibers of a natural polymer. Examples of polymer fibers are fibers of collagen, chitosan, alginate, or hyaluronic acid. The fibers are preferably hydrophilic.

In an embodiment, the tissue repair material comprises polymer fibers. In an embodiment, the tissue repair material comprises collagen fibers. Collagen fibers are fibers of collagen and are insoluble in an aqueous liquid having a pH of 3.5. In an embodiment, the collagen fibers are native collagen fibers, as opposed to reconstituted collagen fibers. In an embodiment, the polymer fibers have an average length of from 1 to 15 mm. In an embodiment, the polymer fibers have an average length of from 0.5 mm to 10 mm. In an embodiment, the polymer fibers have an average length of at least 0.5 mm, at least 1 mm, at least 2 mm, at least 3 mm, or at least 4 mm. In an embodiment, the polymer fibers have an average length of at most 15 mm, at most 12 mm, at most 10 mm, at most 9 mm, at most 8 mm, at most 7 mm, at most 6 mm, at most 5 mm, or at most 4 mm.

Native collagen fibers may have fiber lengths of 50 mm or more. Collagen fiber length may be controlled by known processing methods. For example, average fiber length may be controlled by centrifugal milling of collagen fibers using a cutting head of a suitable gap size. A cutting head gap size of 5 mm yields an average fiber length of about 5 mm. If centrifugal mill cutting head gap size is not known or is substantially non-uniform, average fiber length may be measured using optical comparators or light microscopes.

In an embodiment, the tissue repair material further comprises acid-soluble collagen. Acid-soluble collagen is collagen that is in a form that is insoluble in an aqueous liquid having a pH of 6.5 and is soluble in an aqueous liquid having a pH of 4. To solubilize the collagen in solution, the pH is driven down to between 2 and 4. However, once in solution, the pH can be brought up to 6.5 without coming out of solution. The acid-soluble collagen is introduced into liquid as particles or a powder in order to form the slurry.

In an embodiment, the acid-soluble collagen has been processed without the aid of enzymes and is thus non-enzymatically processed, acid-soluble collagen. Non-enzymatically processed, acid-soluble collagen may be produced by milling a cleaned collagen source material, such as hides or skins. Typically, collagen for use in the invention can be obtained from any suitable animal source, for example, bovine, porcine, piscine, ovine, caprine, or other sources. The tropocollagen resulting from non-enzymatic processing is unable to undergo spontaneous fibrillation under physiological conditions.

In an embodiment, the ratio of collagen fibers to acid-soluble collagen by weight in the tissue repair material is from 25:75 to 75:25. In an embodiment, the tissue repair material comprises from 10 to 75 wt % of acid-soluble collagen and from 25 to 90 wt % of collagen fibers, based on the total amount of collagen in the tissue repair material.

In an embodiment, the tissue repair material is prepared by lyophilizing a composition comprising natural polymer fibers and optionally mineral particles. In an embodiment, the tissue repair material further comprises a mineral. The mineral may be present as particles or fibers. Upon lyophilizing a slurry, the mineral is supported by and retained in the network of polymer fibers. In an embodiment, the mineral is present as particles with an average particle diameter of from 0.05 to 5 mm. In an embodiment, the mineral is present as particles having an average particle diameter of at least 0.05, at least 0.1, at least 0.2, at least 0.3, at least 0.4, or at least 0.5 mm. In an embodiment, the mineral is present as particles having an average particle diameter of at most 5, at most 4, at most 3, at most 2, at most 1, or at most 0.5 mm.

In an embodiment, the mineral comprises hydroxyapatite, bioactive glass, a tricalcium phosphate such as α-tricalcium phosphate or β-tricalcium phosphate, or a bone particle. The bone particle may be anorganic bone particles, autologous bone particles, allogenic bone particles, or xenogenic bone particles, or a combination thereof. The mineral may be monophasic or biphasic. In an embodiment, the tissue repair material comprises from 65, 66, 67, 68, 69, 70, 71, 72, 73, 74, 75, 76, 77, 78, 79, or 80 wt % to 95, 94, 93, 92, 91, 90, 89, 88, 87, 86, or 85 wt % of mineral, based on the total weight of the tissue repair material. In an embodiment, the tissue repair material comprises collagen and a mineral, wherein the collagen is present from 5, 6, 7, 8, 9, 10, 11, 12, 13, 14, or 15 wt % to 30, 29, 28, 27, 26, 25, 24, 23, 22, 21, 20, 19, 18, 17, or 16 wt %, based on the total weight of the tissue repair material.

In an embodiment, the slurry comprises water and polymer fibers. In an embodiment, the slurry further comprises other components, such as acid-soluble collagen or a mineral. The working pH range for a slurry containing collagen fibers and/or acid-soluble collagen is typically from 2 to 8. In an embodiment, the pH of the slurry is from 4.5 to 8. In an embodiment, the slurry further comprises an acid, a base, or a buffer. Generally, the acid or base is added to the slurry to bring the slurry to the desired pH. In the case of a collagen-containing slurry, the viscosity of the slurry is dependent on such factors as the pH of the slurry, the fiber length of collagen fibers, the ratio of fibrous collagen to soluble collagen, and the solids content of the slurry.

In an embodiment, the slurry has a solids content of from 2 to 30 wt %, based on the total weight of the slurry. Solids content is what is left after removing the liquid components of the slurry, for instance after lyophilizing the slurry. In an embodiment, the slurry has a solids content of at least 2, 5, or 10 wt %, based on the total weight of the slurry. In an embodiment, the slurry has a solids content of at most 40, 35, 30, 25, 20, 15, or 10 wt %, based on the total weight of the slurry. The solids content by weight of the slurry will generally be higher when a mineral is present in the slurry than when a mineral is not present in the slurry. In an embodiment, the slurry does not comprise a mineral and the slurry has a solids content of from 2 to 10 wt %. In an embodiment, the slurry comprises a mineral and the slurry has a solids content of from 10 to 40 wt %.

In an embodiment, the tissue repair device or tissue repair material further comprises a bioactive agent. The bioactive agent may be, for example, a steroid, an anti-inflammatory agent, an antibiotic, or another bioactive agent that may be useful to treat a wound or inflammation. The bioactive agent may be present in the interior of the sponge, such as by soaking the sponge in the bioactive agent or by mixing in microparticles comprising the bioactive agent when forming the sponge. The bioactive agent may also be present on an exterior surface by forming a coating on the exterior of the sponge. The coating may be formed by, for example, dissolving a bioactive agent in a degradable synthetic polymer and coating the solution on an exterior surface of the sponge. Suitable degradable synthetic polymers may comprise a polylactic acid (PLA), polyglycolic acid (PGA), poly(lactic-co-glycolic acid) (PLGA), polycaprolactone (PCL), polyester amide (PEA) or a combinations thereof or a co-polymer thereof. In an embodiment, the bioactive agent is present in the hydrating fluid.

In an embodiment, the slurry is introduced into a mold and lyophilized, thereby forming a sponge. This method of forming a sponge generally leads to a sponge having randomly aligned fibers. Following lyophilization, the sponge may be cross-linked. In an embodiment, cross-linking is performed without use of chemicals, such as by dehydrothermally cross-linking a collagen sponge. In an embodiment, cross-linking is performed with the use of chemicals, such as glutaraldehyde.

Using pellets of tissue repair material has the advantage that various sizes of tissue repair device can be formed using the same raw material; greater or fewer pellets are added to the barrel to make tissue repair devices of varying sizes. The pellets may be formed by molding, cutting a sponge into pellets, such as with a laser or knife. In an embodiment, the pellets are molded. In an embodiment, the pellets comprise the shape of a triangular prism, rectangular prism, other polygonal prism, or cylinder. Suitable pellet sizes may be chosen based on the desired flow behavior of the hydrating fluid and the desired packing of the pellets around the obstructions. In an embodiment, a majority of the pellets have a volume of 250, 200, 150, 125, 100, 75, 50, or 40 $mm^3$ or less. In an embodiment, a majority of the pellets have a volume of 25, 30, 35, 40, 45, 50, or 75 $mm^3$ or more. In an embodiment, a majority of the plurality of pellets have a volume of from 30 to 50 $mm^3$.

In an embodiment, the pellets are sized such that they will pass through the tip. In an embodiment, the maximum dimension of the pellets is 6 mm or less, 5 mm or less, or 4 mm or less. In an embodiment, the maximum dimension of the pellets is less than the inner diameter of the tip.

The tissue repair device is typically prepared by first inserting an obstruction into the barrel of the syringe. A side view of the cross-section of such a syringe comprising two obstructions is depicted in FIG. 1. Syringe 1 comprises a barrel 2 and tip 3. Tip 3 is securable to barrel 2 at location 4. The barrel comprises interior wall 5. Elongate obstructions 6 and 7 are positioned within the barrel 2. In an embodiment, the obstruction is a rod. In an embodiment, a barrel contains 1, 2, 3, 4, or 5 obstructions. Elongate obstructions 6 and 7 are inserted into the barrel in direction 8 until they reach the plunger 9. As depicted, each elongate obstruction 4,5 is in contact with the interior wall 5 of barrel 2 over substantially all of the length of the barrel. The obstructions may be present over less than the entire length of the barrel, for instance, if partial filling of the syringe is desired. Typically, the syringe is partially filled by advancing the plunger distally to the desired volume and abutting the obstructions 6 and 7 to plunger 9.

In an embodiment, the elongate obstructions are proximate to the interior wall but are not in contact with the interior wall. The elongate obstructions are positioned proximate to or in contact with the interior wall of the syringe. The obstruction(s) may be connected to a filling cap that is positioned over the syringe to hold the obstructions in place while providing access to the barrel for filling the barrel with tissue repair material.

In an embodiment, channels comprise from 1 to 10% of the total filled volume of the barrel. By total filled volume it is meant the amount of volume of the barrel that would be filled if the barrel were fully filled. For example, if the syringe shown in FIG. 1 has a total capacity in its barrel of 10 cc and the plunger is advanced distally to reduce the capacity to 8 cc, an obstruction inserted into the barrel, and then the barrel filled by adding and compressing tissue repair material, then the total filled volume is 8 cc. In an embodiment, channels comprise at least 1%, 1.5%, or 2% of the total filled volume of the barrel. In an embodiment, channels comprise at most 10%, 9%, 8%, 7%, 6%, 5%, or 4% of the total filled volume of the barrel. In an embodiment, channels comprise from 1.5 to 4% of the total filled volume of the barrel.

Pellets are then added to the barrel to the desired amount of tissue repair material. In an embodiment, the syringe has a volume of from 1 to 15 cubic centimeters. The syringe typically comprises a barrel and a tip. The tip may be a straight, curved, or angled cannula. In an embodiment, the tip comprises a luer lock to allow for attachment of a hydrating syringe in order to insert hydrating fluid into the barrel. In an embodiment, the syringe is a OsteoPrecision™ Bone Graft Delivery Device from Nordson Medical.

After a suitable amount of pellets are added, the tissue repair material may be compressed. For example, a tamper may be used, optionally having one or more holes for the obstructions to pass through. In an embodiment, the pellets are compressed by 5% or more of their volume. By volume it is meant the volume that is taken up by the pellets and the surrounding air in the barrel, which is often easily determined by syringe markings. In an embodiment, the pellets are compressed by at least 10%, 15%, 20%, 25%, 30%, 35%, or 40% by volume. In an embodiment, the pellets are compressed by at most 70%, 60%, or 50%% by volume. In an embodiment, the pellets are compressed from 40% to 60% by volume. The use of pellets may allow better uniformity of compression of the entire volume of the tissue repair material relative to a monolithic sponge.

In an embodiment, the density of the tissue repair material in the barrel prior to hydration is at least 100, 150, 200, or 250 $kg/m^3$. In an embodiment, the density of the tissue repair material in the barrel prior to hydration is at most 400, 350, 325, or 300 $kg/m^3$. In an embodiment, the density of the tissue repair material in the barrel prior to hydration is from 250 to 300 $kg/m^3$. In an embodiment, from 3 to 4.5 g of tissue repair material yields about 9 cc of extrudable tissue repair material. In an embodiment, from 2 to 4 g of tissue repair material yields about 6 cc of extrudable tissue repair material.

In an embodiment, a first quantity of pellets is inserted into the barrel, the first quantity of pellets are compressed. Subsequently, a second quantity of pellets is inserted over the previously compressed first quantity of pellets and the second quantity compressed. Third or further quantities may also be inserted and compressed.

In an embodiment, the compressive force is removed after compressing the pellets and prior to hydration. In an embodiment, the tissue repair material will substantially stay at its compressed volume after removal of the compressive force. In an embodiment, the tissue repair material expands by 10% volume or less, relative to the compressed volume, after the compressive force is removed.

In an embodiment, the compressive force is present at the time of hydration. In such an embodiment the obstructions are removable through, for example a tamper, thereby allowing removal of the obstructions while the compressive force is retained. The hydrating fluid may then be dispensed into the channels, followed by mixing the tissue repair material and hydrating fluid.

Upon removal of the obstruction, a channel is formed defined by a portion of the interior wall of the barrel and the tissue repair material. In an embodiment, the tissue repair material, in its dry state, is sufficiently resistant to flow such that the channel retains substantially consistent volume after the obstruction is removed. This allows for shipping of the tissue repair device without obstructions present in the barrel. In an embodiment, the compressed pellets do not substantially move after removal of the obstruction and compressive force.

Figure 2:
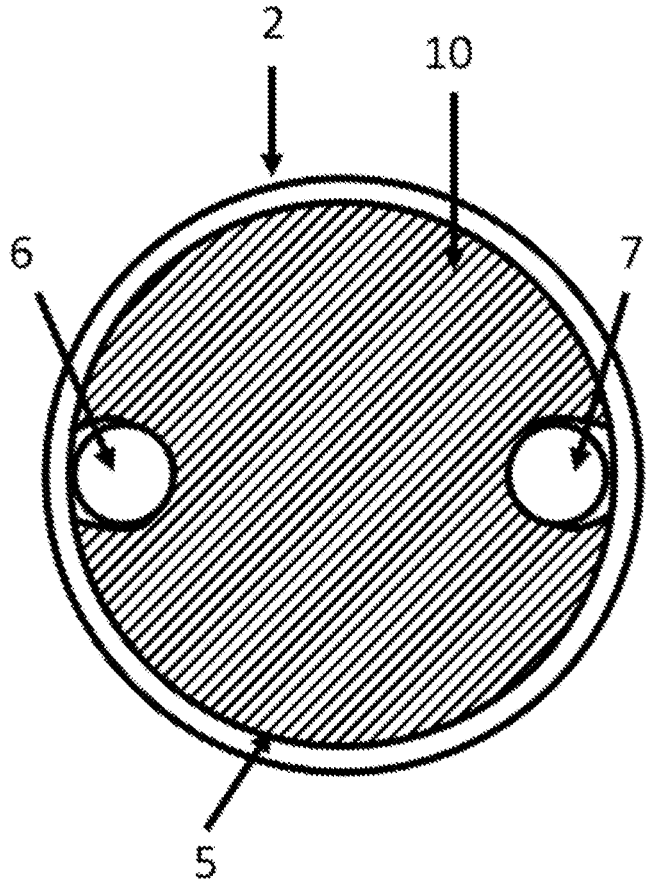
FIG. 2 is a depiction of a top view of a syringe comprising an obstruction.
Figure 3:
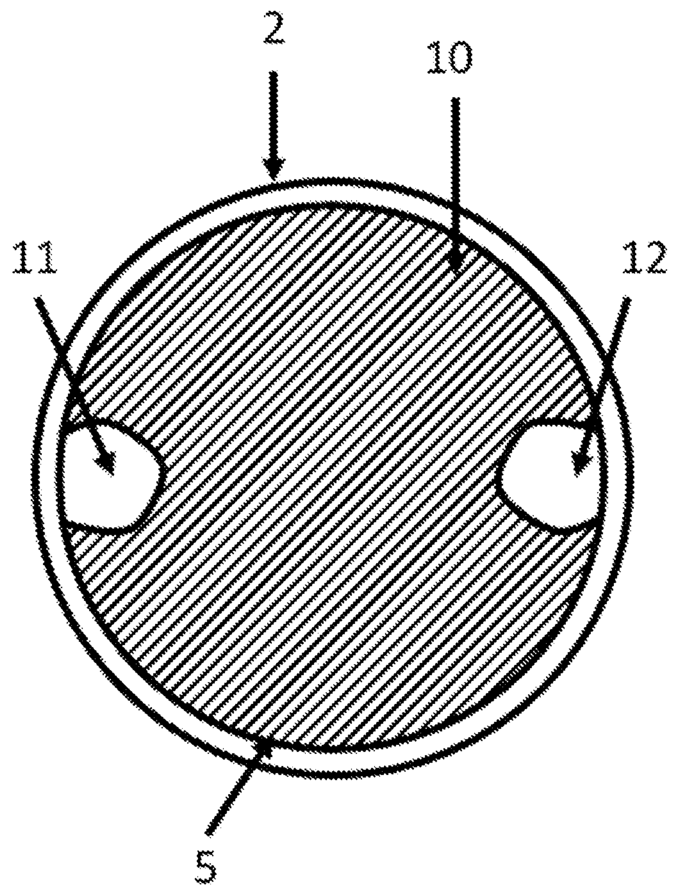
FIG. 3 is a depiction of a top view of a syringe comprising a channel and a tissue repair material.

The pellets typically do not fully fill around the obstruction, allowing for a greater amount of the channel being defined by the interior surface of the barrel than would be assumed had the tissue repair material been a material with a very low viscosity. Thus, the channel is partially defined by the interior surface of the barrel and the compressed tissue repair material. This is depicted in FIG. 2, which is a top view of syringe 1 after pellets of tissue repair material have been inserted into the barrel and the tissue repair material compressed. Tissue repair material 10 flows somewhat around obstructions 6, 7. Upon removal of the obstructions, two channels remain, as depicted in FIG. 3. Channels 11 and 12 are defined by compressed tissue repair material 10 and interior wall 5.

In an embodiment, the hydrating fluid comprises a sterile fluid, saline, whole blood, a constituent of blood such as platelet rich plasma, or bone marrow aspirate. The channels described herein may allow hydrating fluid to flow more easily to the tissue repair material nearest the tip than if dispensing into a channel defined fully by tissue repair material. Preferably, the hydrating fluid and tissue repair material do not require mixing to form a sufficient extrudable tissue repair material. Typically, a dwell time of 30 to 60 seconds after hydrating is sufficient to form the extrudable tissue repair material. Optionally, the hydrating fluid and tissue repair material are mixed. After hydrating, the extrudable tissue repair material may be extruded from the syringe by, for example, actuating a plunger positioned in the barrel.

In an embodiment, the tissue repair device is a bone void filler or suitable for use in filling a defect in bone. In an embodiment, the tissue repair device produces a flowable solution, gel, paste, or putty capable of extrusion from the tip under compressive force manually applied via a plunger.

EXAMPLES

Preparation of Pellets of Tissue Repair Material

An aqueous slurry comprising native, insoluble collagen fibers having an average fiber length of about 5 mm, soluble collagen, and a mineral having a particle size of about 90-600 μm is prepared. The slurry has a solids content of approximately 3.8-4.2 wt %. The slurry is spread into a mold having the shape of a triangular prism having rounded edges. The triangular prism has a base of about 5 mm, a height of about 5 mm, and a depth of about 4 mm. The mold tray is placed in a freeze-dryer and lyophilized. Subsequently, the pellets of tissue repair material are obtained by separating the lyophilized slurry from the mold.

Preparation of Tissue Repair Devices Comprising Pellets

An OsteoPrecision™ Bone Graft Delivery Device from Nordson Medical having a capacity of 15 cc is provided. The tip of the delivery device is separated from the barrel. One or more obstructions, as applicable are added in the forms of a rod having a diameter of 2.4 mm and a height of about 96 mm. The rods are in contact with the interior wall of the barrel. Two rods placed opposite each other are used unless stated otherwise. The volume of a syringe comprising two rods is about 13.8 cc. The configuration is approximately as shown in FIG. 2.

For a 9 cc device the plunger is positioned so that the barrel volume is 15 cc, 1.9 g of pellets of tissue repair material, formed as described above, are placed into the barrel. A rod is used to compress the pellets by hand to approximately 50% of the original volume. Next, 1.9 g of pellets are added on top of the compressed pellets and the pellets compressed again. At this time the barrel is filled with a combination of compressed tissue repair material and obstructions. The obstructions are removed, and the tip of the delivery device is then secured to the barrel. The density of the tissue repair material in the in the barrel just prior to hydration is about 275 kg/m$^3$.

Assessment of Tissue Repair Device Performance

Sufficiency of hydration is assessed by all pellets in the barrel being visually hydrated and surrounded by fluid. In addition, the extruding material is assessed for cohesiveness. If the pellets are sufficiently hydrated the extruding material will exit the syringe as a clean strand; if not sufficiently hydrated, pockets of dry pellets are visible in the extrudate. Moreover, a sufficiently hydrated material will leave behind no dry pellets within the body of the syringe after complete manual depression of the plunger.

Injection force is typically measured by whether the extrudable material is completely injectable by hand without excessive exertion, as opposed to requiring excessive exertion or leaving behind significant amounts of material in the syringe. Injection force may also be assessed using an Instron, positioning the syringe such that the force required to inject the material is measured. The material is suitably injectable by hand if injectable at 21-pound force (93.4 N) or less, which is average one hand strength of an adult.

Example 1—Form of Tissue Repair Material

A first tissue repair device was formed as described under the section Preparation of Tissue Repair Devices Comprising Pellets.

A second tissue repair device was formed similarly. However, instead of the described pellets, four sponges of flat disc shape and having approximate dimensions of height 8 mm, radius of 10 mm are placed into the barrel comprising no rods and compressed. The stacked sponges are not as compressible as the pellets, thereby yielding a tissue repair material density of 192 kg/m$^3$ of tissue repair material just prior to hydration.

A hydrating syringe is attached to the tip of each of the first and second tissue repair devices and the hydrating syringe actuated. Approximately 9 cc of hydrating fluid is dispensed into the barrel. 60 seconds are allowed to elapse before extruding the extrudable tissue repair material.

It was found that the first tissue repair device, comprising pellets, performed superiorly over the second tissue repair device in both sufficiency of hydration of the tissue repair material and injection force.

Example 2—Method of Channel Formation

A first tissue repair device is prepared as described previously under the section Preparation of Tissue Repair Devices Comprising Pellets, but without obstructions.

A second tissue repair device is prepared as described previously, but without obstructions. After loading and compressing of the tissue repair material, 1 rod is forced against the side of the interior wall of the barrel toward the plunger and through the tissue repair material to form one channel.

A third tissue repair device is prepared as described previously, but without obstructions. After loading and compressing of the tissue repair material, 2 rods are forced against the side of the interior wall of the barrel toward the plunger and through the tissue repair material to form two channels.

A fourth tissue repair device is prepared as described previously under the section Preparation of Tissue Repair Devices Comprising Pellets.

A hydrating syringe is attached to the tip of each of the tissue repair devices and the hydrating syringe actuated.

Approximately 9 cc of hydrating fluid is dispensed into the barrel. 60 seconds elapse before extruding the extrudable tissue repair material.

It was found that the second (one rod) and third (two rods) tissue repair devices perform superiorly to the first tissue repair device (no rods). However, the fourth tissue repair device exhibited the best performance in both sufficiency of hydration and injection force, and is more easily assembled than the second and third tissue repair devices.

Example 3—Transportation Stability

To test the dimensional stability of the prepared tissue repair device, the repair device formed previously is placed on a New Brunswick Incubator Shaker Model Innova 44R. The relevant settings are: 45 RPM at 25° C. After 2 hours it was observed that there was no visible dimensional change of the channels. After an additional 24 hours there was still no visible dimensional change, indicating that the formed tissue repair devices may be capable of transportation for commercial use without the obstructions in place.

Example 4—Variation of Channel Location and Volume

Tissue repair device samples are prepared as described previously, but by varying the amount and diameter of the rods to vary the channel quantity and size. The samples are prepared in triplicate according to the following table:

| Sample | Rods | Diameter of each rod (mm) |
|---|---|---|
| 1 | 1 | 1.2 |
| 2 | 1 | 2.4 |
| 3 | 1 | 4.8 |
| 4 | 2 | 1.2 |
| 5 | 2 | 2.4 |
| 6 | 2 | 4.8 |
| 7 | 3 | 1.2 |
| 8 | 3 | 2.4 |
| 9 | 3 | 4.8 |
| 10 | 4 | 1.2 |
| 11 | 4 | 2.4 |
| 12 | 4 | 4.8 |
| CE 1 | 0 | n/a |

The channels are equally spaced, with rods placed in contact with the interior wall of the barrel. The best performing sample will allow for the maximum amount of tissue repair material while yielding sufficient hydration and suitable injection force.

Approximately 1.9-2 g of pellets are placed into the barrel and compressed, followed by placing another 1.9-2 g of pellets in the barrel and compressing again. The tip of the syringe is secured to the barrel. A syringe comprising saline is then attached to the tip and the tissue repair material hydrated at a ratio of 2.25 g water to 1 g of pellets.

The extrudable tissue repair material is assessed for hydration sufficiency and injection force. It is expected that suitable results are obtained with at least one rod over the comparative example. However, it is expected that two rods perform better than one rod, and that two rods perform similarly to three or four rods. Is it also expected that the 2.4 mm diameter rods perform superiorly to the 1.2 mm and 4.8 mm rods.

Additional Description of Exemplary Embodiments

1. A method for forming a tissue repair device comprising the steps of:
   a. providing a syringe comprising a barrel that is configured or configurable to be in fluid communication with a tip, the barrel comprising an interior wall and at least one elongate obstruction extending over a length of the barrel, the obstruction being in contact with or proximate to the interior wall;
   b. inserting into the barrel a plurality of porous, compressible pellets of a tissue repair material, the tissue repair material being extrudable via the tip upon hydration; and
   c. removing the obstruction.
2. A method for forming a tissue repair device comprising the steps of:
   a. providing a syringe comprising a barrel and a tip, the barrel comprising an interior wall, the tip being separated from the barrel and securable to the barrel such that the tip is in fluid communication with the barrel;
   b. placing an obstruction into the barrel, the obstruction being in contact with or proximate to the interior wall of the barrel;
   c. inserting into the barrel a first quantity of porous, compressible pellets of a tissue repair material;
   d. compressing the tissue repair material;
   e. optionally, inserting into the barrel a second quantity of porous, compressible pellets of the tissue repair material, and compressing the second quantity of the tissue repair material; and
   f. removing the obstruction, thereby forming a channel defined by the interior wall of the barrel and the tissue repair material.
3. The method according to any one of the previous exemplary embodiments, further comprising the step of securing the tip to the barrel such that the barrel is in fluid communication with the tip.
4. The method according to any one of the previous exemplary embodiments, further comprising the step of compressing at least some of the plurality of pellets.
5. The method according to any one of the previous exemplary embodiments, further comprising the step of compressing at least some of the plurality of pellets prior to removing the obstruction.
6. The method according to any one of the previous exemplary embodiments, comprising inserting into the barrel a first quantity of pellets, compressing the first quantity of pellets, inserting into the barrel a second quantity of pellets, and compressing the second quantity of pellets.
7. The method according to any one of the previous exemplary embodiments, wherein the obstruction is removed by advancing it proximally from the barrel.
8. The method according to any one of the previous exemplary embodiments, further comprising the step of hydrating the tissue repair material by inserting a hydrating fluid into the channel.
9. The method according to any one of the previous exemplary embodiments, further comprising the step of inserting a hydrating fluid into the channel and mixing the hydrating fluid and the tissue repair material.
10. A method of treating a tissue defect in a human or animal body comprising the steps of:
   a. providing a syringe comprising a barrel in fluid communication with a tip, the barrel comprising an interior wall, tissue repair material, and at least one elongate channel extending over a length of the barrel, the channel being defined by the interior wall and the tissue repair material, wherein the tissue repair material is porous and compressed;

b. inserting a hydrating fluid into the channel to form an extrudable tissue repair material.

11. A method of treating a tissue defect in a human or animal body comprising the steps of:

a. providing a syringe comprising a barrel in fluid communication with a tip, the barrel comprising an interior wall, tissue repair material, and at least one elongate channel extending over a length of the barrel, the channel being defined by the interior wall and the tissue repair material, wherein the tissue repair material is porous and compressed;

b. attaching a second syringe to the tip, the second syringe comprising a hydrating fluid;

c. actuating the second syringe, thereby injecting the hydrating fluid into the barrel of the syringe;

d. waiting until the tissue repair material is sufficiently hydrated, thereby forming an extrudable tissue repair material; and e. extruding the extrudable tissue repair material into a tissue defect of a human or animal body.

12. The method according to any one of the previous exemplary embodiments, wherein the hydrating fluid is inserted into the barrel via the tip.

13. The method according to any one of the previous exemplary embodiments, wherein the hydrating fluid is inserted into the barrel by attaching a second syringe containing the hydrating fluid to the tip and dispensing the hydrating fluid from the second syringe.

14. The method or device according to any one of the previous exemplary embodiments, further comprising a second, third, fourth, fifth, sixth, seventh, eighth, ninth or tenth obstruction.

15. The method or device according to any one of the previous exemplary embodiments, wherein the obstruction is in the form of a cylinder.

16. The method or device according to any one of the previous exemplary embodiments, wherein the obstruction is in the form of a cylinder having a diameter of at least 0.5 mm, 1 mm, 1.5 mm, or 2 mm.

17. The method or device according to any one of the previous exemplary embodiments, wherein the obstruction is in the form of a cylinder having a diameter of at most 10 mm, 9 mm, 8 mm, 7 mm, 6 mm, 5 mm, 4 mm, or 3 mm.

18. The method or device according to any one of the previous exemplary embodiments, further comprising a second, third, fourth, fifth, sixth, seventh, eighth, ninth and/or tenth obstruction, wherein each obstruction is in contact with the interior wall of the barrel.

19. The method or device according to any one of the previous exemplary embodiments, further comprising a second, third, fourth, fifth, sixth, seventh, eighth, ninth and/or tenth channel.

20. The method or device according to any one of the previous exemplary embodiments, further comprising a second, third, fourth, fifth, sixth, seventh, eighth, ninth and/or tenth channel, wherein each channel is defined by the interior wall and the tissue repair material.

21. The method according to any one of the previous exemplary embodiments, further comprising the step of mixing the tissue repair material and the hydrating fluid.

22. The method according to any one of the previous exemplary embodiments, further comprising the step of inserting the extrudable tissue repair device into a tissue defect in a human or animal body.

23. The method according to any one of the previous exemplary embodiments, further comprising the step of injecting the extrudable tissue repair device into a tissue defect in a human or animal body.

24. A tissue repair device comprising: a syringe comprising a barrel in fluid communication with a tip, the barrel comprising an interior wall and a porous, compressed tissue repair material present in the barrel, wherein the tissue repair device is configured such that there is at least one elongate channel extending over a length of the barrel through the tissue repair material, wherein the channel is defined by the interior wall and the tissue repair material.

25. The method or device according to any one of the previous exemplary embodiments, wherein the tissue repair material comprises polymer fibers.

26. The method or device according to any one of the previous exemplary embodiments, wherein the tissue repair material comprises a sponge based on a natural polymer.

27. The method or device according to any one of the previous exemplary embodiments, wherein the sponge is a collagen-based sponge.

28. The method or device according to any one of the previous exemplary embodiments, wherein the tissue repair material comprises fibers of a natural polymer.

29. The method or device according to any one of the previous exemplary embodiments, wherein the tissue repair material further comprises acid-soluble collagen 30. The method or device according to any one of the previous exemplary embodiments, wherein the tissue repair material comprises acid-soluble collagen and collagen fibers.

31. The method or device according to any one of the previous exemplary embodiments, wherein the tissue repair material further comprises a mineral.

32. The method or device according to any one of the previous exemplary embodiments, wherein the tissue repair material further comprises a mineral and the mineral is present as particles having an average particle diameter of from 0.05 to 5 mm, or from 0.05 to 2 mm.

33. The method or device according to any one of the previous exemplary embodiments, wherein the mineral is present as particles having an average particle diameter of at least 0.05, at least 0.1, at least 0.2, at least 0.3, at least 0.4, or at least 0.5 mm.

34. The method or device according to any one of the previous exemplary embodiments, wherein the mineral is present as particles having an average particle diameter of at most 5, at most 4, at most 3, at most 2, at most 1, or at most 0.5 mm.

35. The method or device according to any one of the previous exemplary embodiments, wherein the tissue repair material comprises from 50 to 95 wt % of mineral and from 5 to 50 wt % of collagen, based on the total weight of the dry sponge or the solids of the slurry, respectively.

36. The method or device according to any one of the previous exemplary embodiments, wherein the tissue repair material comprises from 5, 6, 7, 8, 9, 10, 11, 12, 13, 14, or 15 wt % to 30, 29, 28, 27, 26, 25, 24, 23, 22, 21, 20, 19, 18, 17, or 16 wt % of collagen, based on the total weight of the dry sponge or the solids of the slurry, respectively.

37. The method or device according to any one of the previous exemplary embodiments, wherein the tissue repair material comprises from 65, 66, 67, 68, 69, 70, 71, 72, 73, 74, 75, 76, 77, 78, 79, or 80 wt % to 95, 94, 93, 92, 91, 90, 89, 88, 87, 86, or 85 wt % of mineral, based on the total weight of the dry sponge or the solids of the slurry, respectively.
38. The method or device according to any one of the previous exemplary embodiments, wherein the tissue repair material comprises from 10 to 75 wt % of acid-soluble collagen and from 25 to 90 wt % of collagen fibers, based on the total amount of collagen in the dry sponge or slurry, respectively.
39. The method or device according to any one of the previous exemplary embodiments, wherein the ratio of collagen fibers to acid-soluble collagen by weight in the tissue repair material is from 25:75 to 75:25.
40. The method or device according to any one of the previous exemplary embodiments, wherein the tissue repair material is cross-linked.
41. The method or device according to any one of the previous exemplary embodiments, wherein the tissue repair material is formed by lyophilizing a slurry comprising collagen and water.
42. The method or device according to any one of the previous exemplary embodiments, wherein the tissue repair material is formed by lyophilizing a slurry comprising acid-soluble collagen, collagen fibers, and water.
43. The method or device according to any one of the previous exemplary embodiments, wherein the tissue repair material is formed by lyophilizing a slurry comprising acid-soluble collagen, collagen fibers, mineral particles, and water.
44. The method or device according to any one of the previous exemplary embodiments, wherein the tissue repair material comprises acid-soluble collagen is processed without the use of enzymes.
45. The method or device according to any one of the previous exemplary embodiments, wherein the tissue repair material comprises collagen fibers that are native collagen fibers.
46. The method or device according to any one of the previous exemplary embodiments, wherein the tissue repair material comprises polymer fibers having an average length of from 1 to 15 mm.
47. The method or device according to any one of the previous exemplary embodiments, wherein the tissue repair material comprises polymer fibers having an average length of from 0.5 mm to 10 mm.
48. The method or device according to any one of the previous exemplary embodiments, wherein the tissue repair material comprises polymer fibers having an average length of from 1 mm to 5 mm.
49. The method or device according to any one of the previous exemplary embodiments, wherein the tissue repair material comprises polymer fibers having an average length of at least 0.5 mm, at least 1 mm, at least 2 mm, at least 3 mm, or at least 4 mm.
50. The method or device according to any one of the previous exemplary embodiments, wherein the tissue repair material comprises polymer fibers having an average length of at most 15 mm, at most 12 mm, at most 10 mm, at most 9 mm, at most 8 mm, at most 7 mm, at most 6 mm, at most 5 mm, or at most 4 mm.
51. The method according to any one of the previous exemplary embodiments, further comprising the step of forming pellets of tissue repair material.
52. The method according to any one of the previous exemplary embodiments, further comprising the step of forming pellets of tissue repair material by lyophilizing an aqueous slurry in a mold having the shape of a pellet.
53. The method or device according to any one of the previous exemplary embodiments, wherein the pellets are formed by lyophilizing an aqueous slurry in a mold having the shape of a pellet.
54. The method according to any one of the previous exemplary embodiments, further comprising the step of forming pellets of tissue repair material by cutting a sponge comprising polymer fibers.
55. The method or device according to any one of the previous exemplary embodiments, wherein the pellets comprise the shape of a triangular prism, a rectangular prism, other polygonal prism, or a cylinder.
56. The method or device according to any one of the previous exemplary embodiments, wherein a majority of the pellets have a volume of 250, 200, 150, 125, 100, 75, 50, or 40 $mm^3$ or less.
57. The method or device according to any one of the previous exemplary embodiments, wherein a majority of the pellets have a volume of 25, 30, 35, 40, 45, 50, or 75 $mm^3$ or more.
58. The method or device according to any one of the previous exemplary embodiments, wherein a majority of the plurality of pellets have a volume of from 30 to 50 $mm^3$.
59. The method or device according to any one of the previous exemplary embodiments, wherein the plurality of pellets are sized such that they will pass through the tip.
60. The method or device according to any one of the previous exemplary embodiments, wherein the maximum dimension of the pellets is 6 mm or less, 5 mm or less, or 4 mm or less.
61. The method or device according to any one of the previous exemplary embodiments, wherein, the maximum dimension of the pellets is less than the inner diameter of the tip.
62. The method or device according to any one of the previous exemplary embodiments, wherein the barrel has a volume of at least 1, 3, 5, 6, 7, 8, 9, 10, 11, 12, 13, 14, or 15 cubic centimeters.
63. The method or device according to any one of the previous exemplary embodiments, wherein the barrel has a volume of at most 25, 20, 18, 17, 16, or 15 cubic centimeters.
64. The method or device according to any one of the previous exemplary embodiments, wherein the syringe has a maximum volume of 1 to 15 cubic centimeters.
65. The method or device according to any one of the previous exemplary embodiments, wherein the pellets are compressed by at least 10%, 15%, 20%, 25%, 30%, 35%, or 40% by volume.
66. The method or device according to any one of the previous exemplary embodiments, wherein the pellets are compressed by at most 70%, 60%, or 50%% by volume.
67. The method or device according to any one of the previous exemplary embodiments, wherein the pellets are compressed from 40% to 60% by volume.

68. The method or device according to any one of the previous exemplary embodiments, wherein channels comprise from 1 to 10% of the total filled volume of the barrel.
69. The method or device according to any one of the previous exemplary embodiments, wherein channels comprise at least 1%, 1.5%, or 2% of the total filled volume of the barrel.
70. The method or device according to any one of the previous exemplary embodiments, wherein channels comprise at most 10%, 9%, 8%, 7%, 6%, 5%, or 4% of the total filled volume of the barrel.
71. The method or device according to any one of the previous exemplary embodiments, wherein channels comprise from 1.5 to 4% of the total filled volume of the barrel.
72. The method or device according to any one of the previous exemplary embodiments, wherein the density of the tissue repair material in the barrel prior to hydration is from 250 to 300 kg/m$^3$.
73. The method or device according to any one of the previous exemplary embodiments, wherein the density of the tissue repair material in the barrel prior to hydration is at least 100, 150, 200, or 250 kg/m$^3$.
74. The method or device according to any one of the previous exemplary embodiments, wherein the density of the tissue repair material in the barrel prior to hydration is at most 400, 350, 325, or 300 kg/m$^3$.
75. The method or device according to any one of the previous exemplary embodiments, wherein from 3 to 4.5 g of tissue repair material yields about 9 cc of extrudable tissue repair material.
76. The method or device according to any one of the previous exemplary embodiments, wherein from 2 to 4 g of tissue repair material yields about 6 cc of extrudable tissue repair material.
77. The method or device according to any one of the previous exemplary embodiments, wherein the tissue repair material or hydrating fluid further comprises a bioactive agent.
78. The method or device according to any one of the previous exemplary embodiments, wherein the tissue repair material or hydrating fluid further comprises a bone morphogenetic protein, demineralized bone matrix, growth factor, or stem cells.
79. A tissue repair device formed according to the method of any one of the previous exemplary embodiments.
80. A bone void filler formed according to the method of any one of the previous exemplary embodiments.
81. A flowable solution, gel, paste, or putty capable of extrusion formed according to the method of any one of the previous exemplary embodiments.
82. The method or device according to any one of the previous exemplary embodiments, wherein the tissue repair device or tissue repair material is a bone void filler or suitable for use in filling a defect in bone.

The use of the terms “a” and “an” and “the” and similar referents in the context of describing the invention (especially in the context of the following claims) are to be construed to cover both the singular and the plural, unless otherwise indicated herein or clearly contradicted by context. The terms “comprising,” “having,” “including,” and “containing” are to be construed as open-ended terms (i.e., meaning “including, but not limited to,”) unless otherwise noted. Recitation of ranges of values herein are merely intended to serve as a shorthand method of referring individually to each separate value falling within the range, unless otherwise indicated herein, and each separate value is incorporated into the specification as if it were individually recited herein. The use of any and all examples, or exemplary language (e.g., “such as”) provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. While certain optional features are described as embodiments of the invention, the description is meant to encompass and specifically disclose all combinations of these embodiments unless specifically indicated otherwise or physically impossible.

The invention claimed is:

1. A method of forming a tissue repair device comprising the steps of:

a. providing a syringe comprising a barrel that is configured or configurable to be in fluid communication with a tip, the barrel comprising an interior wall, a tissue repair material, and an elongate channel extending over a length of the barrel, the elongate channel being defined by the interior wall and the tissue repair material and the elongate channel being configured such that the tissue repair material does not contact the interior wall within the elongate channel along the length, wherein the tissue repair material comprises porous, compressible pellets and the tissue repair material is porous and compressed; and
b. inserting a hydrating fluid into the elongate channel to form an extrudable tissue repair material.

2. The method according to claim 1, wherein the hydrating fluid is inserted into the barrel by attaching a second syringe containing the hydrating fluid to the tip in fluid communication with the barrel, and dispensing the hydrating fluid from the second syringe into the barrel via the tip.

3. The method according to claim 1, further comprising a second elongate channel positioned opposite the elongate channel, wherein the second elongate channel is defined by the interior wall of the barrel and the tissue repair material and the second elongate channel being configured such that the tissue repair material does not contact the interior wall within the second elongate channel along a length of the second elongate channel.

4. The method according to claim 1, wherein the tissue repair material comprises polymer fibers.

5. The method according to claim 1, wherein the tissue repair material comprises a lyophilized sponge comprising collagen fibers and mineral particles.

6. The method according to claim 1, wherein the mineral is present as particles having an average particle diameter of from 0.05 to 1 mm.

7. The method according to claim 1, wherein the tissue repair material comprises from 50 to 95 wt % of mineral and from 5 to 50 wt % of collagen, based on the total weight of the dry sponge or the solids of the slurry, respectively.

8. The method according to claim 1, wherein the tissue repair material comprises polymer fibers having an average length of from 1 mm to 5 mm.

9. The method according to claim 1, wherein the porous, compressible pellets comprise the shape of a triangular prism, a rectangular prism, other polygonal prism, or a cylinder.

10. The method according to claim 1, wherein the maximum dimension of the porous, compressible pellets is less than the inner diameter of the tip.

11. The method according to claim 1, wherein the porous, compressible pellets are compressed from 40% to 60% by volume.

12. The method according to claim 1, wherein the at least one elongate channel comprises from 1.5 to 4% of the total filled volume of the barrel.

13. A flowable solution, gel, paste, or putty capable of extrusion formed according to the method of claim 1.

14. A tissue repair device comprising: a syringe comprising a barrel in fluid communication with a tip, the barrel comprising an interior wall and a porous, compressed tissue repair material comprising porous, compressible pellets present in the barrel, wherein the tissue repair device comprises an elongate channel extending over a length of the barrel through the tissue repair material, wherein the elongate channel is defined by the interior wall and the tissue repair material, the elongate channel being configured such that the tissue repair material does not contact the interior wall within the elongate channel along the length, and wherein the tissue repair material comprises collagen fibers and mineral particles.

15. The tissue repair device according to claim 14, wherein the at least one elongate channel comprises from 1 to 10% of the total filled volume of the barrel.

16. The tissue repair device according to claim 14, wherein the density of the tissue repair material in the barrel is from 250 to 300 kg/m$^3$.

17. The tissue repair device according to claim 14, wherein the syringe has a maximum volume of 1 to 15 cubic centimeters.

18. The tissue repair device according to claim 14, wherein the maximum dimension of the porous, compressible pellets is 6 mm or less.

19. The tissue repair device according to claim 14, wherein the mineral has an average particle diameter of from 0.05 to 2 mm.

20. The tissue repair device according to claim 14, wherein the tissue repair device comprises two elongate channels, wherein each elongate channel is defined by the interior wall and the tissue repair material, and each elongate channel is configured such that the tissue repair material does not contact the interior wall within each elongate channel along the length.

21. The tissue repair device according to claim 20, wherein each of the two elongate channels has a diameter of from 2 to 5 mm.

22. The method of claim 1, further comprising the steps of:

a. extruding the extrudable tissue repair material, thereby forming an extruded tissue repair material, and b. inserting the extruded tissue repair material into a tissue defect in a human or animal body.

23. A method for forming a tissue repair device comprising the steps of:

a. providing a syringe comprising a barrel that is configured or configurable to be in fluid communication with a tip, the barrel comprising an interior wall and at least one elongate obstruction extending over a length of the barrel, the at least one elongate obstruction being in contact with or proximate to the interior wall;

b. inserting into the barrel a plurality of porous, compressible pellets of a tissue repair material, the tissue repair material being extrudable via the tip upon hydration;

c. compressing at least some of the plurality of porous, compressible pellets; and d. removing the at least one elongate obstruction.

* * * * *